United States Patent
Quan et al.

(10) Patent No.: US 12,246,321 B2
(45) Date of Patent: Mar. 11, 2025

(54) NANOSENSOR METHODS AND APPARATUSES FOR DETERMINATION OF ANALYTES

(71) Applicant: President and Fellows of Harvard College, Cambridge, MA (US)

(72) Inventors: Qimin Quan, Cambridge, MA (US); Feng Liang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 572 days.

(21) Appl. No.: 16/644,148

(22) PCT Filed: Sep. 7, 2018

(86) PCT No.: PCT/US2018/049883
§ 371 (c)(1),
(2) Date: Mar. 3, 2020

(87) PCT Pub. No.: WO2019/051181
PCT Pub. Date: Mar. 14, 2019

(65) Prior Publication Data
US 2021/0001330 A1    Jan. 7, 2021

Related U.S. Application Data

(60) Provisional application No. 62/556,186, filed on Sep. 8, 2017.

(51) Int. Cl.
*B01L 3/00* (2006.01)
*G01N 21/25* (2006.01)
*G01N 21/552* (2014.01)

(52) U.S. Cl.
CPC .......... *B01L 3/5085* (2013.01); *G01N 21/25* (2013.01); *G01N 21/554* (2013.01);
(Continued)

(58) Field of Classification Search
None
See application file for complete search history.

(56) References Cited

U.S. PATENT DOCUMENTS 3,779,628 A   12/1973  Kapron
5,457,041 A   10/1995  Ginaven
(Continued)

FOREIGN PATENT DOCUMENTS

CN   104487824 A   4/2015
CN   205679617 U   11/2016
(Continued)

OTHER PUBLICATIONS

Soo et al., A simple gold nanoparticle probes assay for identification of *Mycobacterium tuberculosis* and *Mycobacterium tuberculosis* complex from clinical specimens, Molecular and Cellular Probes 23, available online May 20, 2009, pp. 240-246. (Year: 2009).*
(Continued)

*Primary Examiner* — Rebecca M Giere
(74) *Attorney, Agent, or Firm* — Wolf, Greenfield & Sacks, P.C.

(57) ABSTRACT

The present invention generally relates, in some aspects, to articles and methods relating to nanosensors for determination of molecules and other features, e.g., via surface plasmonic resonance, electric resonance, magnetic resonance, color changes, or the like. These articles and methods may be used, for example, for sample detection. The articles described in some aspects of the invention include a microwell array and a nanosensor array. In some embodiments, The nanosensor arrays may utilize nanoparticles positioned on nanostructures that are able to interact with a sample suspected of containing an analyte, such as a single cell. The interaction between nanoparticles and a sample can be detected by a change in applied energy, such as altered electromagnetic radiation caused by surface plasmonic reso-
(Continued)

nance of incident visible light, and/or other types of resonance. Electromagnetic radiation may be applied to a microwell array and nanosensor, and the applied electromagnetic radiation may be altered as a nanosensor interacts with a sample suspected of containing an analyte.

21 Claims, 22 Drawing Sheets

(52) U.S. Cl.
CPC .............. *B01L 2200/0647* (2013.01); *B01L 2200/141* (2013.01); *B01L 2300/044* (2013.01); *B01L 2300/0829* (2013.01); *B01L 2300/0893* (2013.01); *B01L 2300/0896* (2013.01); *B01L 2300/123* (2013.01); *G01N 2201/06113* (2013.01)

(56) References Cited

U.S. PATENT DOCUMENTS

| | | |
|---|---|---|
| 6,506,564 B1 | 1/2003 | Mirkin et al. |
| 6,645,757 B1 | 11/2003 | Okandan |
| 2002/0028519 A1 | 3/2002 | Yguerabide et al. |
| 2003/0112443 A1 | 6/2003 | Hjelme |
| 2003/0138819 A1 | 7/2003 | Gong et al. |
| 2004/0012062 A1 | 1/2004 | Miyajima et al. |
| 2004/0134884 A1 | 7/2004 | Wei et al. |
| 2004/0182707 A1 | 9/2004 | Kent |
| 2004/0183176 A1 | 9/2004 | Naya et al. |
| 2005/0117157 A1 | 6/2005 | Tarsa |
| 2005/0161594 A1 | 7/2005 | Hollingsworth |
| 2007/0087436 A1 | 4/2007 | Miyawaki et al. |
| 2007/0090836 A1 | 4/2007 | Xiang et al. |
| 2007/0220882 A1 | 9/2007 | Culepepper et al. |
| 2007/0256480 A1 | 11/2007 | Black et al. |
| 2010/0016174 A1 | 1/2010 | Kim |
| 2010/0124824 A1 | 5/2010 | Eilmsteiner et al. |
| 2010/0297686 A1 | 11/2010 | Gogotsi et al. |
| 2011/0207237 A1 | 8/2011 | Sai |
| 2011/0208031 A1 | 8/2011 | Wolfe |
| 2011/0237445 A1 | 9/2011 | Svahn et al. |
| 2011/0277249 A1 | 11/2011 | Abuzaina et al. |
| 2012/0045748 A1 | 2/2012 | Willson et al. |
| 2013/0137129 A1 | 5/2013 | Yu et al. |
| 2013/0244895 A1 | 9/2013 | Voros et al. |
| 2013/0286467 A1 | 10/2013 | Vlasko-Vlasov et al. |
| 2013/0319123 A1 | 12/2013 | Wang et al. |
| 2013/0338627 A1 | 12/2013 | Rylander et al. |
| 2014/0024131 A1 | 1/2014 | Kim et al. |
| 2014/0218727 A1 | 8/2014 | Li et al. |
| 2014/0322729 A1 | 10/2014 | Fan et al. |
| 2014/0334005 A1 | 11/2014 | Omenetto et al. |
| 2014/0358128 A1 | 12/2014 | Montazeri et al. |
| 2015/0092191 A1 | 4/2015 | Jung |
| 2015/0118124 A1 | 4/2015 | Khorasaninejad et al. |
| 2015/0226738 A1 | 8/2015 | Dai et al. |
| 2016/0003744 A1 | 1/2016 | Chou et al. |
| 2016/0299134 A1 | 10/2016 | Denomme et al. |
| 2016/0312275 A1 | 10/2016 | Blainey et al. |
| 2016/0355869 A1 | 12/2016 | Blair et al. |
| 2017/0265788 A1 | 9/2017 | Quan et al. |
| 2017/0284935 A1 | 10/2017 | Nudukaife et al. |

FOREIGN PATENT DOCUMENTS

| | | |
|---|---|---|
| CN | 106233140 A | 12/2016 |
| CN | 106841188 A | 6/2017 |
| JP | 2006-288406 A | 10/2006 |
| JP | 2011-152108 A | 8/2011 |
| JP | 2014-531043 A | 11/2014 |
| JP | 2015-514225 A | 5/2015 |
| JP | 2016-29400 A | 3/2016 |
| JP | 2017-503483 A | 2/2017 |
| KR | 20160128213 A | 11/2016 |
| WO | WO 2004/086044 A1 | 10/2004 |
| WO | WO 2007/022026 A2 | 2/2007 |
| WO | WO 2008/116093 A2 | 9/2008 |
| WO | WO 2013/062540 A1 | 5/2013 |
| WO | WO 2013/154770 A1 | 10/2013 |
| WO | WO 2014/021809 A1 | 2/2014 |
| WO | WO 2013/100373 A2 | 7/2015 |
| WO | WO 2015/130980 A1 | 9/2015 |
| WO | WO 2015/175398 A1 | 11/2015 |
| WO | WO 2016/125106 A1 | 8/2016 |
| WO | WO 2016/168386 A1 | 10/2016 |
| WO | WO 2017/124101 A2 | 7/2017 |

OTHER PUBLICATIONS

International Search Report and Written opinion mailed Aug. 7, 2015 for Application No. PCT/US2015/030125.
International Preliminary Report on Patentability mailed Nov. 24, 2016 for Application No. PCT/US2015/030125.
Invitation to Pay Additional Fees mailed Apr. 2, 2018 for Application No. PCT/US18/13313.
International Search Report and Written opinion mailed Jun. 1, 2018 for Application No. PCT/US18/13313.
International Preliminary Report on Patentability mailed Jul. 25, 2019 for Application No. PCT/US18/13313.
Invitation to Pay Additional Fees mailed Nov. 1, 2018 for Application No. PCT/US18/49883.
International Search Report and Written opinion mailed Jan. 29, 2019 for Application No. PCT/US18/49883.
International Preliminary Report on Patentability mailed Mar. 19, 2020 for Application No. PCT/US18/49883.
Gautam et al., Adsorption kinetics of ammonia sensing by graphene films decorated with platinum nanoparticles. Journal of Applied Physics. May 11, 2012;111:094317.
Goncalves et al., Self-Assembled Hydrogel Nanoparticles for Drug Delivery Applications. Materials. Feb. 2, 2010; 3:1420-1460.
Hosokawa et al., Nanoparticle Technology Handbook Elsevier. Oct. 19, 2017; Science. 644 pages. p. 365.
Hsieh et al., Localized surface plasmon coupled fluorescence fiber-optic biosensor with gold nanoparticles. Anal Chem. May 1, 2007;79(9):3487-93. Epub Mar. 23, 2007.
Kundu et al., Development of evanescent wave absorbance-based fibre-optic biosensor. Pramana—J Phys. Dec. 2010;75: 1099. doi:10.1007/s12043-010-0193-6.
Lepinay et al., Improved detection limits of protein optical fiber biosensors coated with gold nanoparticles. Biosens Bioelectron. Feb. 15, 2014;52:337-44. doi: 10.1016/j.bios.2013.08.058. Epub Sep. 14, 2013.
Lin et al., Tapered optical fiber sensor based on localized surface plasmon resonance. Opt Express. Sep. 10, 2012;20(19):21693-701. doi: 10.1364/OE.20.021693.
Szunerits et al., Sensing using localised surface plasmon resonance sensors. Chem Commun (Camb). Sep. 18, 2012;48(72):8999-9010. doi: 10.1039/c2cc33266c. Epub Jul. 17, 2012.
Wei et al., Sensitive plasmonic biosensor using gold nanoparticles on a nano fiber tip. Proc. SPIE 6099. Plasmonics in Biology and Medicine III. Feb. 2006;60990J doi:10.1117/12.642541.
Partial European Search Report mailed Mar. 17, 2021 for Application No. EP 18854207.0.
Notice of Supplemental European Search Report mailed Jul. 6, 2021 for Application No. EP 18854207.0.
Extended European Search Report mailed Jun. 18, 2021 for Application No. EP 18854207.0.
Chinese Office Action mailed May 5, 2022 for Application No. CN 201880066841.9.
Japanese Office Action mailed Jul. 5, 2022 for Application No. JP 2020-513860.
Kim et al., Interfacing silicon nanowires with mammalian cells. J Am Chem Soc. Jun. 13, 2007;129(23):7228-9. doi: 10.1021/ja071456k. Epub May 22, 2007.

(56) References Cited

OTHER PUBLICATIONS

Makvandi et al., Engineering Microneedle Patches for Improved Penetration: Analysis, Skin Models and Factors Affecting Needle Insertion. Nano-Micro Latters. Nov. 16, 2020;13(93):1-41.
Ryu et al., Nanoneedle insertion into the cell nucleus does not induce double-strand breaks in chromosomal DNA. J Biosci Bioeng. Sep. 2013;116(3):391-6. doi: 10.1016/j.jbiosc.2013.03.022. Epub May 3, 2013.
Chinese Office Action mailed Oct. 19, 2022 for Application No. CN 201880066841.9.
Chinese Office Action mailed Mar. 16, 2023 for Application No. CN 201880066841.9.
Japanese Office Action mailed Nov. 22, 2022 for Application No. JP 2020-513860.
Langer et al., Present and Future of Surface-Enhanced Raman Scattering. ACS Nano. Jan. 28, 2020;14(1):28-117. doi: 10.1021/acsnano.9b04224. Epub Oct. 8, 2019.
Japanese Office Action mailed Jul. 11, 2023 for Application No. 2023-045563.
CN 201880066841.9, Mar. 16, 2023, Chinese Office Action.
JP 2020-513860, Nov. 22, 2022, Japanese Office Action.
Chinese Office Action mailed Aug. 31, 2023 for Application No. CN 201880066841.9.
Nath et al., A colorimetric gold nanoparticle sensor to interrogate biomolecular interactions in real time on a surface. Anal Chem. Feb. 1, 2002;74(3):504-9. doi: 10.1021/ac015657x.
CN 201880066841.9, Aug. 31, 2023, Chinese Office Action.
Japanese Office Action mailed Jan. 9, 2024 for Application No. JP 2023-045563.
U.S. Appl. No. 15/310,253, filed Nov. 10, 2016, Quan et al.
CN 201880066841.9, Feb. 1, 2024, Chinese Office Action.
Chinese Office Action mailed Feb. 1, 2024 for Application No. CN 201880066841.9.
Wang, Application of a multifunctional composite material based on Gold Nanorods (GNRs) in the diagnosis and treatment of oral cancer. Chinese Doctoral Dissertations Full-text Database Engineering Science and Technology I. Jul. 2016;(7):30-37.
Chinese Office Action mailed Aug. 24, 2024 for Application No. CN 201880066841.9.
Japanese Office Action mailed Aug. 6, 2024 for Application No. JP 2023-045563.
Gierahn et al., Seq-Well: portable, low-cost RNA sequencing of single cells at high throughput. Nat Methods. Apr. 2017;14(4):395-398. doi: 10.1038/nmeth.4179. Epub Feb. 13, 2017.
JP 2023-045563, Jan. 9, 2024, Japanese Office Action.
Extended European Search Report mailed Oct. 10, 2024 for Application No. EP 24190029.9.

\* cited by examiner

NANOSENSOR METHODS AND APPARATUSES FOR DETERMINATION OF ANALYTES

RELATED APPLICATIONS

This application is a national stage filing under 35 U.S.C. § 371 of International Patent Application Serial No. PCT/US2018/049883, filed Sep. 7, 2018, which claims the benefit of U.S. Provisional Patent Application Ser. No. 62/556,186, filed Sep. 8, 2017, entitled "Nanosensor Methods and Apparatuses for Determination of Analytes," by Quan, et al., each of which is incorporated herein by reference in its entirety.

TECHNICAL FIELD

The present invention generally relates, in some aspects, to articles and methods relating to nanosensors for determination of molecules and other features, e.g., via surface plasmonic resonance, color changes, or the like.

BACKGROUND

Immunoassays have been extensively used for disease diagnostics. Conventional immunoassays (e.g., enzyme-linked immunosorbent assay, western blot) have limited detection sensitivity typically at 100 pg/ml and above, due to the bulk measurement of fluorescent or colorimetric signals derived from fluorescently labeled molecules or enzymatic reactions. In addition, current immunoassays can only be performed on a large number of cells. Existing single cell technology includes flow cytometry, which is limited by the choice of antibodies, as typical flow cytometry methods are only compatible with 10% of available antibodies. None of the current available technologies can detect intracellular molecules at the single cell level in a highly-multiplexed format.

Accordingly, improvements in detection limits are needed for disease prognostics and drug development.

SUMMARY

The present invention generally relates, in some aspects, to articles and methods relating to nanosensors for determination of molecules and other features, e.g., via surface plasmonic resonance, electric dipole resonance or magnetic dipole resonance, color changes, or the like. The subject matter of the present invention involves, in some cases, interrelated products, alternative solutions to a particular problem, and/or a plurality of different uses of one or more systems and/or articles.

In one aspect, the present invention is generally directed to an article. In one set of embodiments, the article comprises a microwell array comprising a well comprising a nanoparticle positioned distally on an end of a nanostructure, wherein the nanoparticle interacts with incident light via surface plasmonic resonance, electric resonance, and/or magnetic resonance.

According to another set of embodiments, the article comprises a microwell array comprising a well, and a nanosensor array comprising a nanoparticle positioned distally on the end of a nanostructure contained within the well, wherein the nanoparticle is sized to interact with incident visible light via surface plasmonic resonance, electric resonance, and/or magnetic resonance to alter the incident visible light.

In another aspect, the present invention is generally directed to a method. In another set of embodiments, a method of assembling the article is described. The method comprises immobilizing a first substrate comprising a microwell array comprising a well relative to a second substrate comprising an array of nanostructures, at least some of the nanostructures comprising nanoparticles positioned distally on an end of the nanostructures, such that the nanostructures are positioned within the wells.

In one set of embodiments, the method comprises applying electromagnetic radiation to a nanoparticle positioned distally on an end of a nanostructure, wherein the nanoparticle interacts with the electromagnetic radiation via surface plasmonic resonance, electric resonance, and/or magnetic resonance to alter the electromagnetic radiation, and determining the altered electromagnetic radiation.

The method, in accordance with another set of embodiments, comprises positioning a cell within a well of a microwell array, wherein the well further comprises a nanoparticle positioned distally on the end of a nanostructure and a reaction entity at least partially coated on the nanoparticle. In another set of embodiments, the method further comprises lysing the cell within the well to release an analyte suspected of being able to bind the reaction entity, and applying electromagnetic radiation to the nanoparticle, wherein the nanoparticle interacts with the electromagnetic radiation via surface plasmonic resonance, electric resonance, and/or magnetic resonance to alter the electromagnetic radiation, and determining the altered electromagnetic radiation to determine the analyte.

Still another set of embodiments relates to a method comprising acquiring a first optical image of an array of nanostructures on a substrate, wherein the nanostructures have a cross-sectional dimension, orthogonal to the direction that the first optical image is acquired, of less than 700 nm, and wherein the nanostructures are at least partially coated with a reaction entity. In another set of embodiments, the method further comprises causing an interaction between the reaction entity and an analyte, acquiring a second optical color image of the array of nanostructures, and determining a change in color between the first optical image and the second optical image, wherein the change in color is caused by the interaction between the reaction entity and the analyte.

In one set of embodiments, the method comprises positioning a sample in a well of a microwell array, wherein the well further comprises a nanoparticle positioned distally on the end of a nanostructure, and applying electromagnetic radiation to the nanoparticle, wherein the nanoparticle interacts with the electromagnetic radiation via surface plasmonic resonance, electric resonance, and/or magnetic resonance to alter the electromagnetic radiation, and determining the altered electromagnetic radiation.

Another set of embodiments is a method comprising adding a sample suspected of containing an analyte to a well of a microwell array, wherein the well further comprises a nanoparticle positioned distally on an end of a nanostructure, the nanoparticle being at least partially coated with a reaction entity. In another set of embodiments, the method comprises applying electromagnetic radiation to the nanoparticle, wherein the nanoparticle interacts with incident light via surface plasmonic resonance, electric resonance, and/or magnetic resonance to alter the electromagnetic radiation, and determining the altered electromagnetic radiation to determine the interaction of the reaction entity with the analyte.

In another set of embodiments, a method comprises exposing a solution suspected of containing an analyte to a nanoparticle positioned distally on the end of a nanostructure, wherein the nanostructure further comprises a reaction entity able to interact with the analyte, applying electromagnetic radiation to the nanoparticle, wherein the nanoparticle interacts with the electromagnetic radiation via surface plasmonic resonance, electric resonance, and/or magnetic resonance to alter the electromagnetic radiation, and determining the altered electromagnetic radiation.

The method, according to another set of embodiments, comprises acquiring first and second optical color images of an array of nanostructure on a substrate, wherein the nanostructure have a cross-sectional dimension of between 400 nm and 700 nm, and determining a change in color between the first and second optical color images.

Other advantages and novel features of the present invention will become apparent from the following detailed description of various non-limiting embodiments of the invention when considered in conjunction with the accompanying figures.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates, in some aspects, to articles and methods relating to nanosensors for determination of molecules and other features, e.g., via surface plasmonic resonance, electric resonance, magnetic resonance, color changes, or the like. These articles and methods may be used, for example, for sample detection. The articles described in some aspects of the invention include a microwell array and a nanosensor array. In some embodiments, the nanosensor arrays may utilize nanoparticles positioned on nanostructures that are able to interact with a sample suspected of containing an analyte, such as a single cell. The interaction between nanoparticles and a sample can be detected by a change in applied energy, such as altered electromagnetic radiation caused by surface plasmonic resonance of incident visible light, and/or other types of resonance. Electromagnetic radiation may be applied to a microwell array and nanosensor, and the applied electromagnetic radiation may be altered as a nanosensor interacts with a sample suspected of containing an analyte. In addition, in some embodiments, the nanosensor arrays may utilize nanostructures and the binding of analytes may be determined based on optical or color changes.

Certain aspects of the invention are generally directed to systems and methods for detecting biomolecules such as proteins or nucleic acids, e.g., arising from cells or other sources. In some embodiments, biomolecules are determined, qualitatively and/or quantitatively, using nanoneedle or other nanostructures used as sensors. These may be present, for example, within an array, such as an array of wells.

In one set of embodiments, a particle on an end of the nanoneedle has a narrow band spectrum. Binding of biomolecules or other analytes to the particle, e.g., via reaction entities, may affect the ability of the particle to resonate to incident light, e.g., due to surface plasmon resonance, electric resonance, and/or magnetic resonance. Examples of reaction entities include antibodies, enzymes, nucleic acids, or other entities such as those described below. By determining differences in resonance, e.g., by applying light to the particles and determining refraction and/or absorbance, binding interactions may be determined for the particles and the biomolecules.

Figure 1:
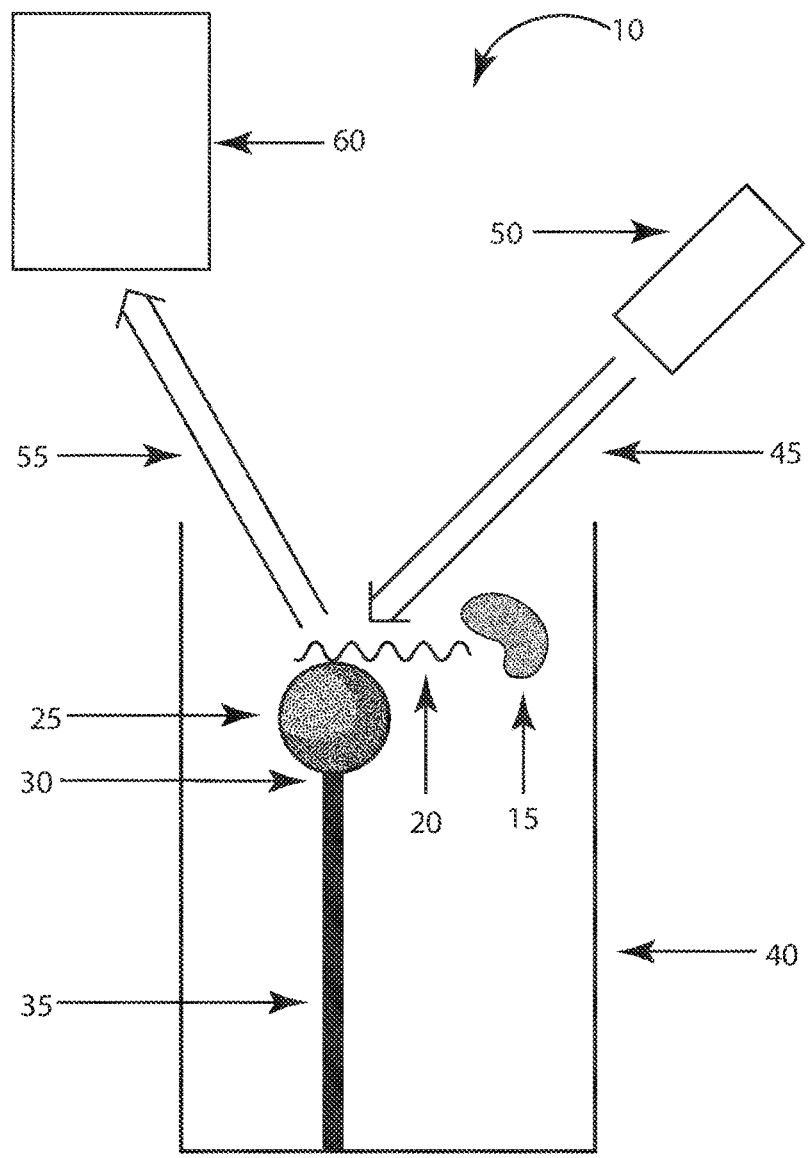
FIG. 1 shows, according to some embodiments, an illustration of the interaction between nanosensor and analyte, which alters incident electromagnetic radiation.

As a non-limiting example, FIG. 1 shows system 10, in which an analyte 15 may interact with a reaction entity 20 immobilized relative to a nanoparticle 25. The interaction may be, for example specific or non-specific, covalent or non-covalent, etc. Nanoparticle 25 may be positioned at the end 30 of a nanoneedle 35 or other suitable nanostructure. In some cases, the nanoneedle may be positioned in a well 40 (for example, an isolated well or a well of a microarray, etc.), although in other cases, the nanoneedle may be positioned on a substrate, optionally on a suitable nanostructure, and not necessarily within a well. Incident light 45 from source 50 may interact with nanoparticle 25 and may interact with the particle via the plasmonic resonance effect. In addition, some light 55 may be directed to a detector 60, e.g., via refraction from the particle. By determining differences in the light reaching the detector, various interactions between analyte 15 and reaction entity 20 may be determined.

In another set of embodiments, binding of biomolecules or other analytes can be determined using changes in color, e.g., visible light. Without wishing to be bound by any theory, it is believed that certain types of nanoneedles or other nanostructures are able to vibrate (e.g., in response to visible light) only at a fundamental mode. The fundamental mode may change, for example, upon binding of a biomolecule to the nanoneedle, e.g. due to a reaction entity. Accordingly, changes in the visible properties of the nanoneedles (for example, color and/or intensity changes) may be used to determine binding interactions between the nanoneedles and the biomolecules.

Figure 2A:
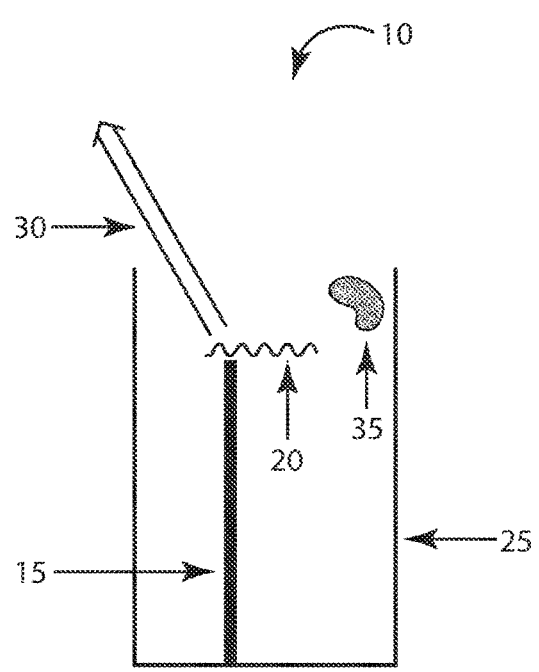
FIGS. 2A-2B show, according to some embodiments, the change in visible light produced by a nanosensor upon binding an analyte.
Figure 2B:
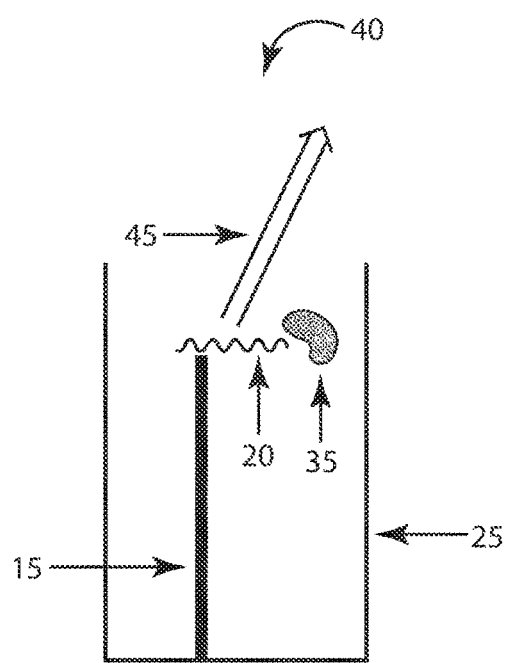

As a non-limiting example, FIG. 2A shows system 10, in whichnanoneedle 15 and reaction entity 20 positioned in well 25 produce color of visible light 30. Analyte 35 does not interact with nanoneedle 15 or reaction entity 20, and produces no visible light. In system 40 in FIG. 2B, nanoneedle 15 and reaction entity 20 positioned in well 25 bind analyte 35. The interaction results in a change of optical color or appearance, produced by visible light 45, that may different from visible light 30.

In some cases, the biomolecules (or other analytes) arise from cells. For example, cells may be lysed within wells of a microwell plate, and determined, qualitatively and/or quantitatively, using nanoneedle or other nanostructures used as sensors as discussed herein. In some cases, particles may also be present. The biomolecules may be determined using plasmonic resonance effects, color changes, or the like, e.g., as described herein. In some cases, cells may be introduced into particles and sealed therein, e.g., using membranes. The cells can be individually lysed within separate wells, e.g., to prevent contamination of one well with another well from cell lysates. In some cases, semi-permeable membranes are used to allow the entry of lysing reagent (e.g., a lysing buffer) to enter the wells, but to prevent the lysate from leaving the wells. Thus, the lysates of individual cells may be individually determined according to certain embodiments.

Figure 3:
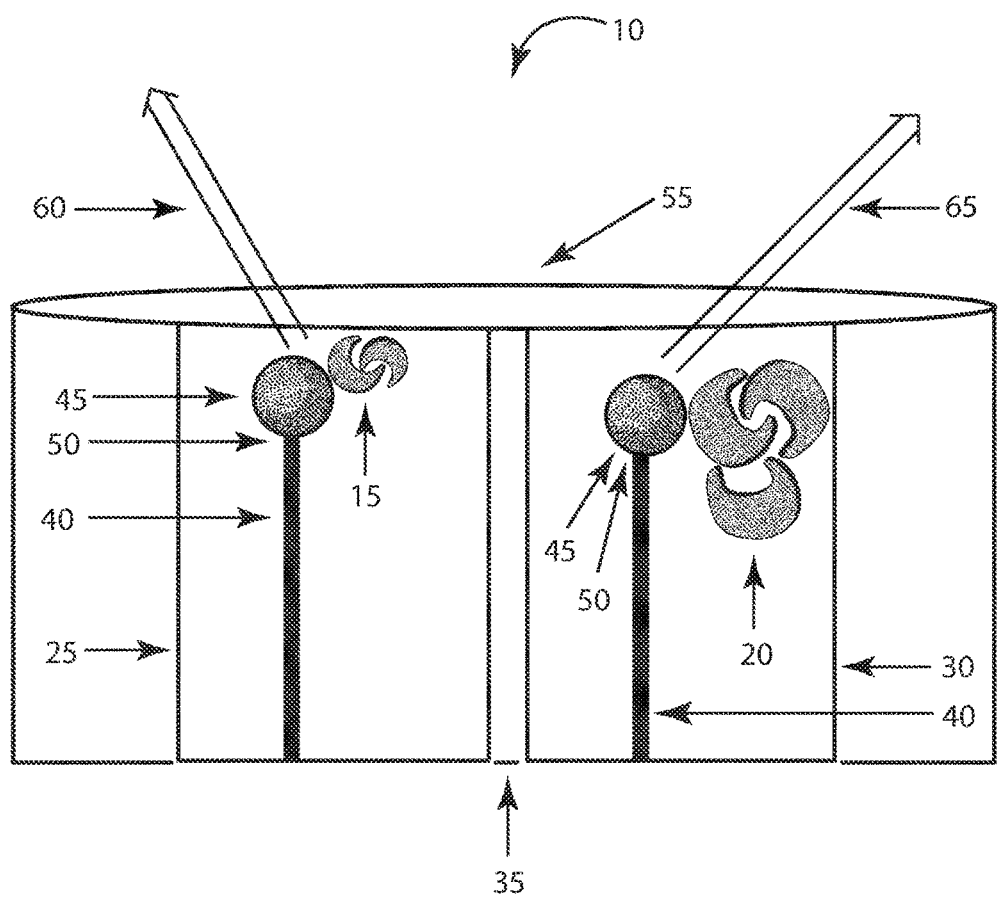
FIG. 3 shows, according to some embodiments, a microwell array with a semipermeable membrane comprising a nanosensor and various concentrations of analyte, which produce optical light.
Figure 4:
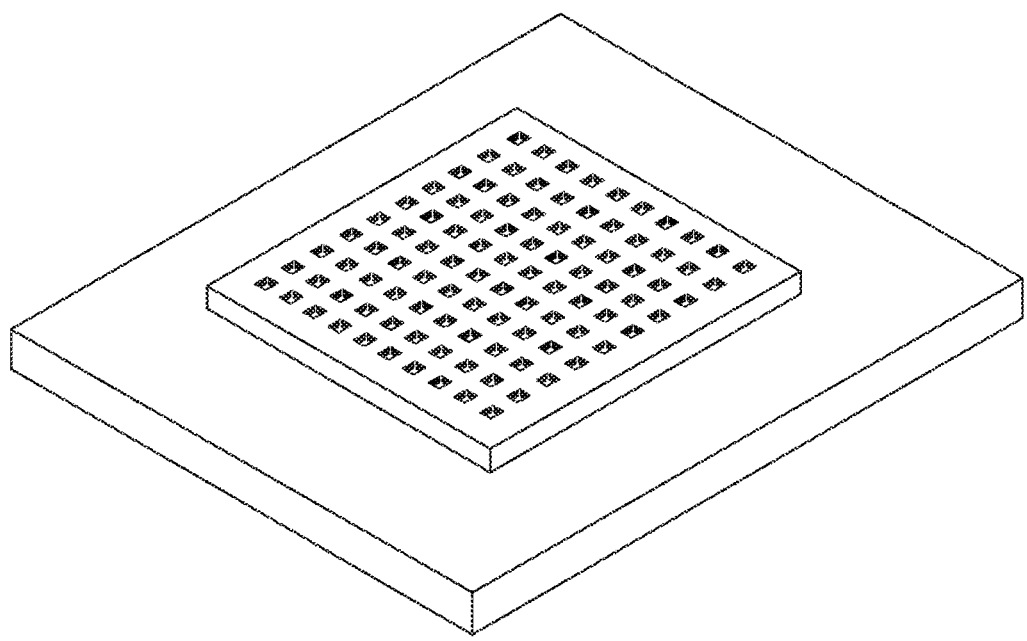
FIG. 4 shows, according to some embodiments, an illustration of a microwell array.
Figure 5:
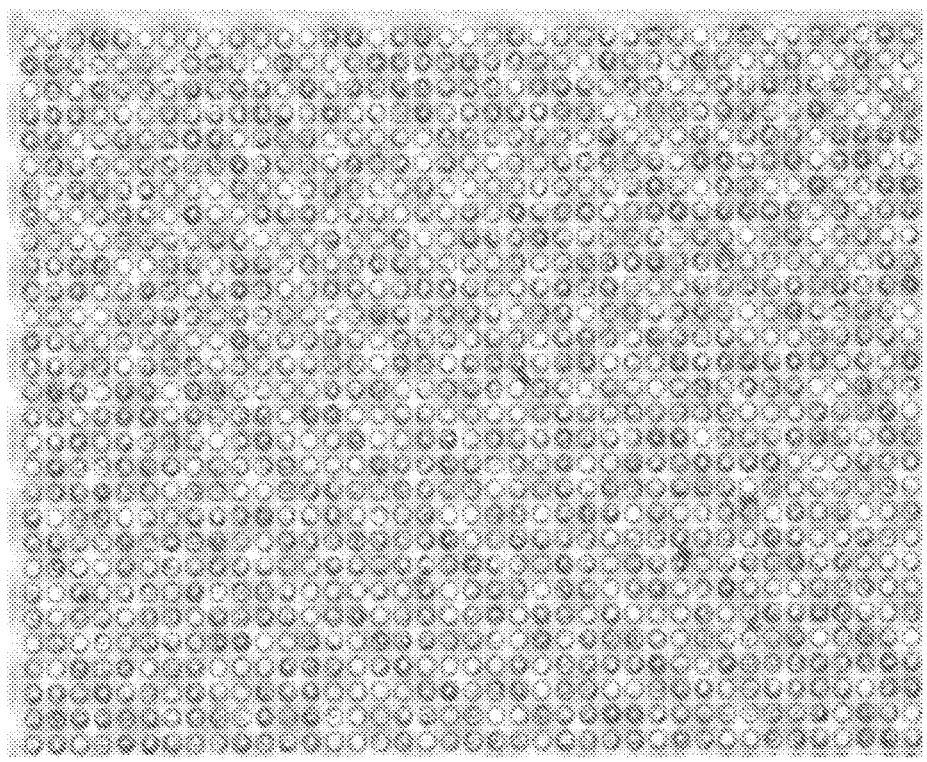
FIG. 5 shows an exemplary representation of the trapping of HEK293 cells at about 70% single cell trapping efficiency.

FIG. 3 displays a non-limiting example of system 10, including wells 25 and 30. Cell 15 and cell 20 are positioned within wells 25 and 30, respectively. Cell 15 and 20 may be lysed, for example, upon the addition of lysing buffer into wells 25 and 30. Positioned on microwell array 35 is semi-permeable membrane 55 to prevent contamination of the contents of well 25 and well 30. The semi-permeable membrane may be added, for example, after introduction of the cells into the wells, and before or after lysis of the cells.

The interaction of nanoparticle 45 with analytes from cell 15 may result in optical light 60, while the interaction of nanoparticle 45 with analytes from cell 20 (more concentrated than cell 15) may result in optical light 65. For example, incident light may be applied, and some of the light may be absorbed by the nanoneedles. Differences in analytes (e.g., concentrations, types, etc.) may result in different optical light or appearances of the different wells or nanoneedles. As another example, the wells may comprise nanosensors comprising nanoneedle 40 and nanoparticle 45 positioned on the end 50 of nanoneedle 35. Incident light may interact with such systems by the plasmonic resonance effect, which may result in different refracted light or appearances based on different interactions between analytes and nanoparticles (e.g., via reaction entities). By determining such light, the analytes may be determined.

The above represents various non-limiting examples of certain embodiments of the invention. However, other embodiments are also possible. Accordingly, more generally, various aspects of the invention are now described in relation to nanosensors for determination of molecules and other features, e.g., via surface plasmonic resonance, color changes, or the like.

Some articles and methods of the present invention relate to a sensor comprising a particle (e.g., a nanoparticle) that is positioned on a nanostructure, e.g., distally on an end of the nanostructure. In some cases, the particle can interact with an analyte, e.g., as discussed below, such that interactions between the analyte and the nanostructure and/or the particle can be determined (e.g., qualitatively and/or quantitatively) by determining how light interacts with the particle. For example, light may interact with the particle via surface plasmon resonance effects, and changes in the light may be used to determine the analyte. In some cases, other resonances may occur, such as electrical resonances and/or magnetic resonances.

A variety of samples may be determined in various embodiments of the invention. For example, in certain aspects, a sample may comprise a cell. The nanosensor may be used to optically interrogate or study a sample, for example, a cell. In some cases, a characteristic of the cell or other sample, such as the presence or concentration of an analyte or sample, may interact with the nanosensor and/or a reaction entity on the nanosensor, which can be determined optically. Examples of optical interrogation techniques that may be used include, but are not limited to, fluorescence, phosphorescence, surface plasma resonance, surface plasmonic resonance, localized surface plasma resonance, Raman spectroscopy, surfaced-enhanced Raman spectroscopy, or the like.

In certain embodiments, the nanoparticle comprises a metal, for example, gold, silver, copper, or the like. According to some embodiments, the nanoparticle comprises gold. In another set of embodiments, the nanoparticle comprises silver, a quantum dot, or a semiconductor nanoparticle.

In some embodiments, the particles are sized to interact with incident visible light via the surface plasmonic resonance effect, e.g., to alter the incident visible light. For example, some of the incident light may be absorbed, reflected, refracted, etc. upon interaction with a particle.

This may produce changes in the light, which may be determined in some fashion. In addition, in some cases, the particles are sized to interact with incident visible light via electric and/or magnetic resonance effects.

In some cases, the particle may be a nanoparticle. For example, the particle may have a characteristic diameter of less than about 1 micrometer. The particle may be spherical or nonspherical. The characteristic diameter may be taken as the diameter of a perfect sphere having the same volume as the nonspherical particle. According to certain embodiments, the diameter of the nanoparticle is at least 0.5 nm, at least 1.0 nm, at least 1.5 nm, at least 2.0 nm, at least 2.5 nm, at least 3 nm, at least 4 nm, at least 5 nm, at least 7 nm, at least 10 nm, at least 30 nm, at least 100 nm, at least 300 nm, etc. In some embodiments, the diameter of the nanoparticle is less than 1000 nm, less than 500 nm, less than 300 nm, less than 100 nm, less than 50 nm, less than 30 nm, less than 10 nm, less than 7 nm, less than 5 nm, less than 4 nm, less than 3.0 nm, less than 2.5 nm, less than 2.0 nm, less than 1.5 nm, or less than 1.0 nm. In addition, combinations of any of these are also possible; for example, the characteristic diameter may be in a range of 0.5 to 3.0 nm.

In some embodiments, the particle and/or the nanostructure is at least partially coated with a reaction entity. The term "reaction entity" refers to any entity that can interact with an analyte in such a manner to cause a detectable change in a property, e.g., of a member, such as a chemical property, an optical property, a mechanical property, a vibration property, etc. The interaction between the reaction entity and the analyte may be specific or non-specific binding, and may include a variety of interactions. Interaction of the reaction entity with an analyte may be determinable as discussed herein, e.g., due to a change in light.

The reaction entity can comprise a binding partner to which the analyte binds in some embodiments. The reaction entity can comprise a specific or a non-specific binding partner of the analyte. For example, the reaction entity may be a chemical or a biochemical, such as a metal, a nucleic acid, an antibody, an aptamer, a sugar, a carbohydrate, a protein, a polymer, an oligonucleotide, a catalyst, a quantum dot, etc. As a non-limiting example, in certain embodiments, the reaction entity at least partially coating the nanoparticle is an antibody or fragment thereof. The antibody may be any suitable antibody, including monoclonal antibodies, chimeric antibodies, humanized antibodies, etc. In some embodiments, the reaction entity comprises an enzymatic reaction product induced by a chromogenic substrate labeled on the analyte. Chromogenic substrates may include, for example, 3,3',5,5'-tetramethylbenzidine (TMB), 3,3'-diaminobenzidine (DAB), 2,2'-azino-di-(3-ethylbenzthiazoline-6-sulfonic acid) (ABTS), and the like.

The binding partner may be a molecule that can undergo binding with a particular analyte, and includes specific, semi-specific, and non-specific binding partners as is known to those of ordinary skill in the art. The term "specifically binds," when referring to a binding partner (e.g., protein, aptamer, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies that specifically bind to their antigen, and the like. The binding may be by one or more of a variety of mechanisms including, but not limited to, ionic interactions, covalent interactions, hydrophobic interactions, van der Waals interactions, and/or hydrogen bonding, etc.

As another example, the reaction entity may comprise platinum, which can be used to determine hydrogen. As yet another example, the reaction entity may comprise a hydrogel, which can be used to determine water or humidity. Non-limiting examples of reaction entities include those disclosed in Int. Pat. Apl. Pub. No. WO 2015/175398, incorporated herein by reference in its entirety for all purposes.

In some cases, one or more particles may be immobilized relative to a nanostructure, e.g., directly or indirectly, for example, via one or more linkers or spacers. For example, the particles may be attached to any suitable location on the nanostructure, such as a side or an end. As an example, the nanostructures may be attached to a substrate at a first end, and a particle may be attached to a second end distal from the first end.

The nanostructure may have any suitable shape and/or size. In some cases, for example, the nanostructure may be a nanoneedle, a nanowire, a nanorod, a nanocone, or the like. See, e.g., FIG. 8. Other shapes are also possible, e.g., nanoribbons, nanofilaments, nanotubes, nanopillars, or the like. In certain embodiments, the nanostructures are vertically aligned, although other angles or alignments are also possible.

In some embodiments, the nanostructure has a length, determined from an end or a point of attachment with a substrate, of less than about 100 micrometers, less than about 50 micrometers, less than about 30 micrometers, less than about 20 micrometers, less than about 10 micrometers, less than about 5 micrometers, less than about 3 micrometers, less than about 2 micrometers, less than about 1 micrometer, less than about 500 nm, less than about 300 nm, less than about 200 nm, less than about 100 nm, less than about 50 nm, less than about 30 nm, less than about 20 nm, less than about 10 nm, etc. In some cases, the length may be at least about 10 nm, at least about 20 nm, at least about 30 nm, at least about 50 nm, at least about 100 nm, at least about 200 nm, at least about 300 nm, at least about 500 nm, at least about 1 micrometer, at least about 2 micrometers, at least about 3 micrometers, at least about 5 micrometers, at least about 10 micrometers, at least about 20 micrometers, at least about 30 micrometers, at least about 50 micrometers, at least about 100 micrometers, etc. Combinations of any of these are possible, e.g., the length of the nanostructure may be between 0.2 to 2 micrometers.

The nanostructure may have any suitable cross-sectional shape, for example, square, circular, triangular, ellipsoidal, polygonal, a star, an irregular shape, etc. The nanostructure may maintain the same cross-sectional shape throughout its length, or there may be different cross-sectional shapes in different portions of the nanostructure. In addition, the nanostructures may have any suitable cross-sectional diameter. The cross-sectional diameter may be constant (e.g., as in a nanoneedle or a nanorod), or varying (for example, as in a nanocone). The average diameter may be, for example, less than about 1000 nm, less than about 500 nm, less than about 300 nm, less than about 200 nm, less than about 100 nm, less than about 50 nm, less than about 30 nm, less than about 20 nm, less than about 10 nm, etc. In some cases, the length may be at least about 10 nm, at least about 20 nm, at least about 30 nm, at least about 50 nm, at least about 100 nm, at least about 200 nm, at least about 300 nm, at least about 500 nm, at least about 1000 nm, etc. Combinations are also possible in various embodiments. For example, the average diameter of the nanostructure may be between 50 nm and 300 nm.

The nanostructure may be formed out of any suitable material, and may be the same or different from a substrate upon which it is attached, e.g., vertically. In one set of embodiments, the nanostructures are formed from silicon and/or other suitable semiconductive materials (for example, germanium). Addition non-limiting examples of materials include metals (e.g., nickel or copper), silica, glass, or the like. In some cases, the nanostructure (which may be attached to a substrate) can be formed from a unitary material.

Any suitable method may be used to from the nanostructure. Examples include, but are not limited to, lithographic techniques such as e-beam lithography, photolithography, X-ray lithography, extreme ultraviolet lithography, ion projection lithography, etc. As another example, in some embodiments, the nanostructure may be formed from one or materials that are susceptible to etching with a suitable etchant. For instance, the nanostructure may comprise materials such as silica or glass, which can be etched using HF (hydrofluoric acid) or BOE (buffered oxide etch). As another example, the nanostructure may comprise a metal such as copper, iron, nickel, and/or steel, which can be etched using acids such as HCl (hydrochloric acid), $HNO_3$ (nitric acid), sulfuric acid ($H_2SO_4$), and/or other etching compounds such as such as ferric chloride ($FeCl_3$) or copper sulfate ($CuSO_4$). As yet another example, the nanostructure may comprise silicon or other semiconductor materials, which can be etched using etchants such as EDP (a solution of ethylene diamine and pyrocatechol), KOH (potassium hydroxide), and/or TMAH (tetramethylammonium hydroxide). The nanostructure may also comprise, in some cases, a plastic or a polymer, for example, polymethylmethacrylate, polystyrene, polyperfluorobutenylvinylether, etc., which can be etched using KOH (potassium hydroxide), and/or other acids such as those described herein.

The nanostructure may comprise or consist essentially of one material, or more than one material in some embodiments. For instance, in one embodiment, the nanostructure is formed from a unitary or a solid piece of material that may be etched as discussed herein.

Certain embodiments of the invention are also generally related to microwell arrays, e.g., which comprises one or more wells, which may be circular or non-circular. Any number of wells may be present, for example, at least 1, at least 2, at least 5, at least 10, at least 25, at least 50, at least 100, at least 200, at least 500, etc. The microwells may also comprise one or more sensors as described herein, e.g., comprising one or more nanoneedles or other nanostructures. In some embodiments, the microarrays are dimensioned according to commercially-available ANSI/SLAS standards, e.g., with 6 wells, 12 wells, 24 wells, 48 wells, 96 wells, 384 wells or 1536 wells, etc. The microwell arrays may be formed out of any suitable material, including plastics or polymers, such as polystyrene, polypropylene, polycarbonate, cyclo-olefin, etc., silica, glass, metals, or the like.

In certain embodiments, a well may have a diameter in a range of 10 microns to 50 microns. According to some embodiments of the invention, the diameter of the well is at least 10 microns, at least 20 microns, at least 30 microns, or at least 40 microns. In certain embodiments, the diameter of the well is less than 50 microns, less than 40 microns, less than 30 microns, or less than 20 microns. Combinations of any of these are also possible, e.g., the well may have a diameter of 20 to 40 microns.

According to certain embodiments, the depth of the well is at least 20 microns, at least 30 microns, at least 40 microns, or at least 50 microns. In certain aspects of the invention, the depth of the well is less than 60 microns, less than 50 microns, less than 40 microns, or less than 30 microns. Combinations of any of these are also possible, e.g., a well may have a depth in a range of 20 microns to 60 microns.

In some embodiments, the wells may have a pitch (or a well-to-well spacing) of no more than about 1000 micrometers, no more than about 700 micrometers, no more than about 500 micrometers, no more than about 300 micrometers, no more than about 100 micrometers, no more than about 50 micrometers, no more than about 40 micrometers, no more than about 30 micrometers, no more than about 25 micrometers, no more than about 20 micrometers, no more than about 15 micrometers, no more than about 10 micrometers, no more than about 5 micrometers, no more than about 3 micrometers, no more than about 2 micrometers, no more than about 1 micrometer, etc. In some cases, the pitch may be at least about 1 micrometer, at least about 3 micrometers, at least about 5 micrometers, at least about 10 micrometers, at least about 15 micrometers, at least about 20 micrometers, at least about 25 micrometers, at least about 30 micrometers, at least about 40 micrometers, at least about 50 micrometers, at least 100 micrometers, at least 300 micrometers, at least 500 micrometers, at least 700 micrometers, at least 1000 micrometers, etc. In addition, combinations of any of these are also possible; for example, the pitch may be between about 10 micrometers and 100 micrometers.

In some cases, the microwell array may be configured to contain one or more cells. For example, one or more lysates arising from a cell may be determined in one or more wells, using one or more sensors as described herein. However, it should be understood that cells (or cell lysates) are not required, and other embodiments of the invention may be directed to lysates arising from other sources, including biological and non-biological analytes.

In some cases, the microwell array may be loaded to have one cell per well, or more than one cell per well. Different wells may have the same or different numbers of cells that are present. The cell may be an isolated cell, a cell aggregate, or a cell found in a cell culture, in a tissue construct containing cells, or the like. Examples of cells include, but are not limited to, a bacterium or other single-cell organism, a eukaryotic cell, a plant cell, or an animal cell. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a human or non-human mammal. If the cell is from a multicellular organism, the cell may be from any part of the organism.

In some embodiments, one or more cells are added to one or more wells, and optionally sealed in place (e.g., to prevent contamination or interaction between different wells), for example, using a membrane such as a semipermeable membrane. According to some embodiments, however, cells may be lysed within the wells to release one or more analytes of interest, such as proteins, nucleic acids, or the like.

A variety of techniques may be used to lyse cells. For instance, the cells may be lysed via exposure to a lysing chemical or a cell lysis buffer (e.g., a surfactant such as Triton-X or SDS, an enzyme such as lysozyme, lysostaphin, zymolase, cellulase, mutanolysin, glycanases, proteases, mannase, proteinase K, etc.), or a physical condition (e.g., ultrasound, ultraviolet light, mechanical agitation, etc.). If a lysing chemical is used, the lysing chemical may be added to the wells before and/or after adding cells. In some cases, the lysing chemical may be added before or after adding a membrane, e.g., to contain the cell within the well. In some cases, the membrane is permeable and/or semipermeable, which may facilitate entry of the lysing chemical.

Some embodiments of the invention generally relate to a semi-permeable membrane that can be applied to the microwell array and/or nanostructure substrate, for example, to contain cells or other samples within the wells. In certain cases, the semi-permeable membrane is sized so as to prevent the passage of cells but allow the passage of smaller compounds.

In certain embodiments of the invention, a semi-permeable membrane can be positioned between the microwell array and the nanostructure substrate, or on top of the microwell array or the nanostructure substrate. In some cases, the semi-permeable membrane can be removed from the microwell array and/or the nanostructure substrate. In certain embodiments, the semi-permeable membrane is evaluated by microscopy, such as dark field microscopy or other optical microscopy techniques.

A variety of semi-permeable membranes may be used, e.g., having various permeabilities. For instance, the semi-permeable membrane may be hydrophilic or hydrophobic, porous or nonporous, etc. In certain embodiments, the semi-permeable membrane may comprise polymers such as polycarbonate. Other examples of semipermeable membranes include cation exchange membranes, anion exchange membranes, or the like.

As previously mentioned, embodiments of the articles and methods may include a nanostructure substrate that directly or indirectly relates to the microwell array. In some embodiments of the invention, the nanostructure substrate comprises multiple nanosensors that are described herein. According to certain embodiments, the microwell array and the nanostructure substrate are separable. In some cases, separation may be performed without the use of tools. In other embodiments of the invention, the microwell array and the nanostructure substrate are inseparable. In certain embodiments of the invention, the microwell array and nanostructure substrate are directly attached to each other, for example, such that a nanosensor is present in at least one well of the microwell array.

In some embodiments, light may be applied to the nanosensor, e.g., to determine an analyte as discussed herein. In some cases, the light may interact with the nanosensor (for example, a nanoparticle in the nanosensor) via surface plasmonic resonance, and/or other resonances such as electric and/or magnetic resonances, and the effect of the interaction may be determined, for example, by determining refraction and/or absorbance of the light. In one set of embodiments, the light applied to the nanosensor may be an incident beam comprising plane polarized light from a laser, such as a He—Ne laser. Other lasers are also commercially available.

In some cases, the incident light strikes a substrate surface, such as a silicon surface or metal surface (e.g., gold), for example of a particle. In some cases, interaction of an analyte with the nanosensor (e.g., via a reaction entity) may alter the refractive index, or other characteristics, of the incident light, and this may be determined, e.g., using a detector. For example, in certain embodiments, localized surface plasmonic oscillations can produce optical changes to the nanosensors, which may, for instance, generate absorptions within the ultraviolet and/or visible light regions. These can be determined and used to determine binding or other interactions between an analyte and a reaction entity, such as a protein or nucleic acid.

In some cases, the light may be detected with a microscope and/or a spectrometer, or other optical detector. A variety of suitable optical detectors, including spectrometers, are commercially available. In some cases, there may be other optical components present, e.g., to facilitate interactions or detection. Examples of optical components include, but are not limited to, a waveguide, an optical sensor, an optical detector, an optical fiber, or the like.

However, it should be understood that other methods of detection are available in addition to, or instead of, surface plasmonic resonance effects such as those described herein. For example, in some embodiments, analytes may interact with reaction entities immobilized relative to a nanostructure (i.e., which may or may not have a particle such as a nanoparticle), and changes in optical appearance, for example, a change in color, may be determined to determine binding of the analyte to the reaction entities. Any suitable method may be used to determine changes in optical appearance, for example, optical microscopy, spectrofluorimetry, or the like.

In certain embodiments of the invention, an analyte can interact with a nanosensor causing changes in optical appearance as the nanosensor interacts with incident light via electric resonance or magnetic resonance. Without wishing to be bound by any theory, electric resonance or magnetic resonance may occur upon interaction of light with a nanosensor or portion thereof, such as a nanoparticle. In some cases, the resonances may be altered, for example, upon application of a suitable electrical field or magnetic field. A variety of electric and/or magnetic field generators are readily available commercially.

In some cases, the distance or pitch between nanostructures in a periodic structure may be controlled, for example, such that the nanostructures form a meta-surface. For example, the pitch may be set to be less than the wavelength of the incident light. For instance, the pitch may be less than 700 nm, less than 600 nm, less than 500 nm, etc. and/or greater than 400 nm, greater than 500 nm, or greater than 600 nm. For instance the pitch may be between 400 nm and 500 nm. The nanostructures may have any of the dimensions provided herein. In some cases, the average cross-sectional diameter of the nanostructure is less than the wavelength of the incident light.

Without wishing to be bound by any theory, scattered light from the individual nanostructures may interfere, and the amount of interference may be sensitive to the analytes or other entities bound to the nanostructures. In this way, changes in color or other optical properties may be used to determine changes in analyte interactions.

It should be understood that other pitches may be used, for example, when applying infrared or ultraviolet light. For instance, the pitch may be less than 1000 nm, less than about 500 nm, less than about 300 nm, less than about 200 nm, less than about 100 nm, less than about 50 nm, less than about 30 nm, less than about 20 nm, less than about 10 nm, etc. and/or the pitch may be at least about 10 nm, at least about 20 nm, at least about 30 nm, at least about 50 nm, at least about 100 nm, at least about 200 nm, at least about 300 nm, at least about 500 nm, at least about 1000 nm, etc. Combinations of any of these are also possible in various embodiments.

Int. Pat. Apl. Pub. No. WO 2015/175398 is incorporated herein by reference in its entirety. In addition, U.S. Provisional Patent Application Ser. No. 62/556,186, filed Sep. 8, 2017, entitled "Nanosensor Methods and Apparatuses for Determination of Analytes," by Quan, et al. is also incorporated herein by reference in its entirety.

The following examples are intended to illustrate certain embodiments of the present invention, but do not exemplify the full scope of the invention.

EXAMPLE 1

Figure 6:
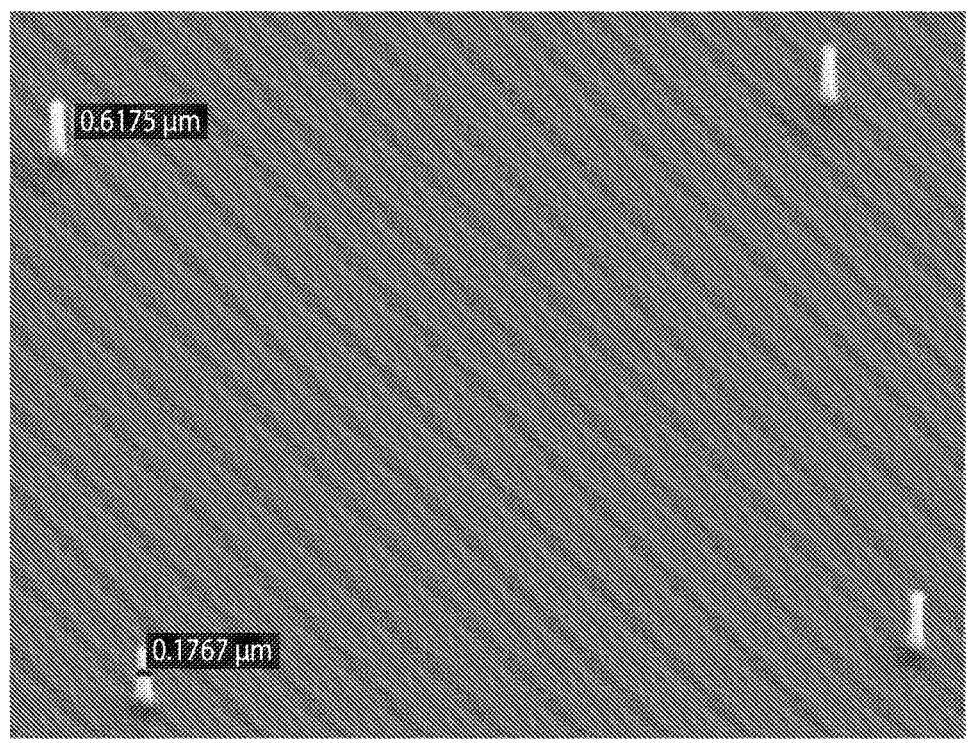
FIG. 6 shows an exemplary representation of silicon nanorod nanosensors.
Figures 7A, 7B:
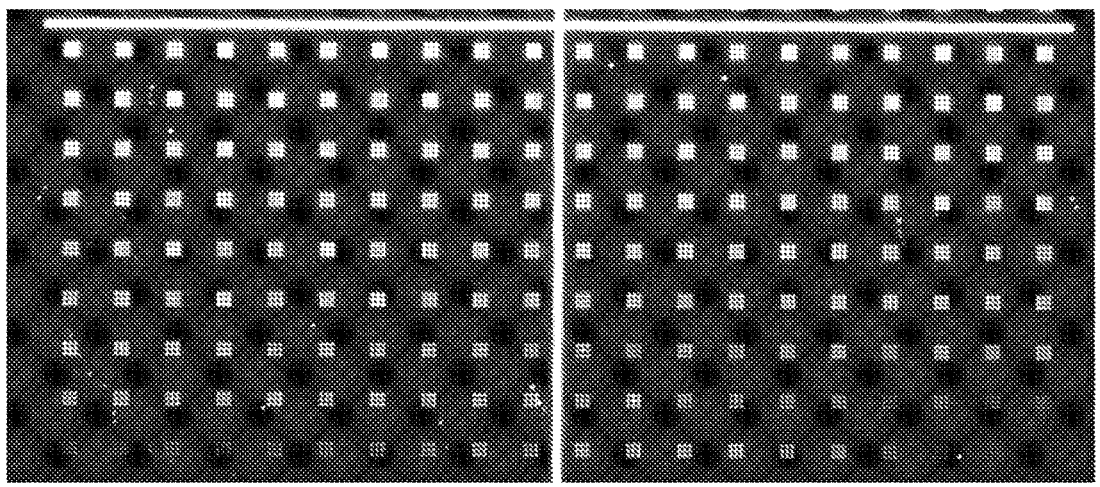
FIGS. 7A-7B show exemplary representations of the color of silicon nanorods under a dark field image.
Figure 8A:
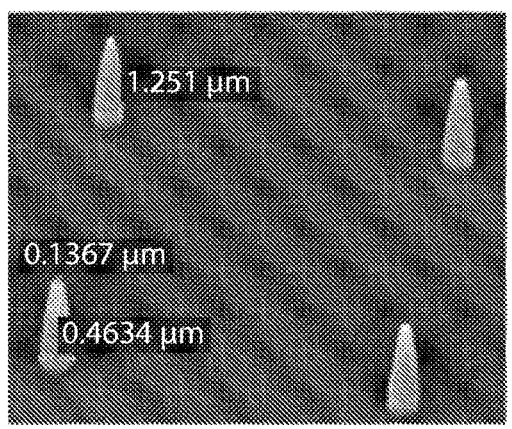
FIGS. 8A-8D show, according to some embodiments, multiple forms of silicon nanosensors, including nanocones, nanoneedles, nanowires, and nanoparticles.
Figure 8B:
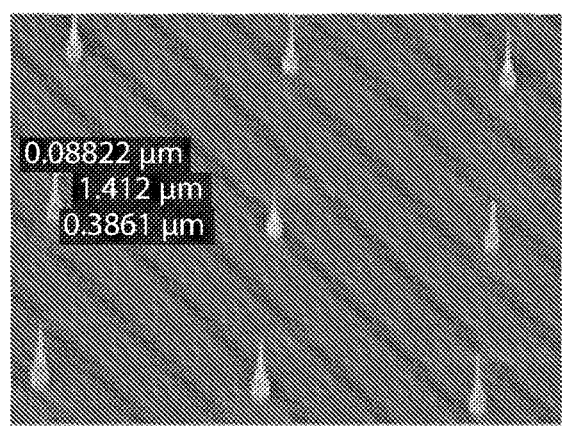
Figure 8C:
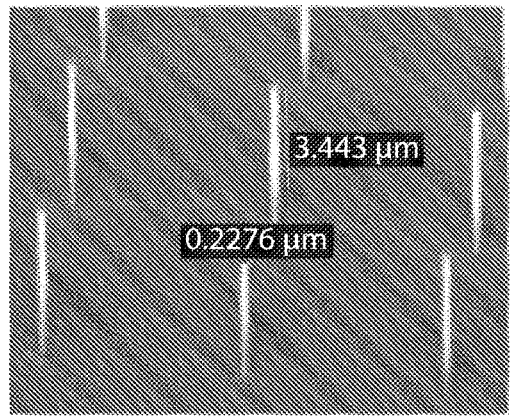
Figure 8D:
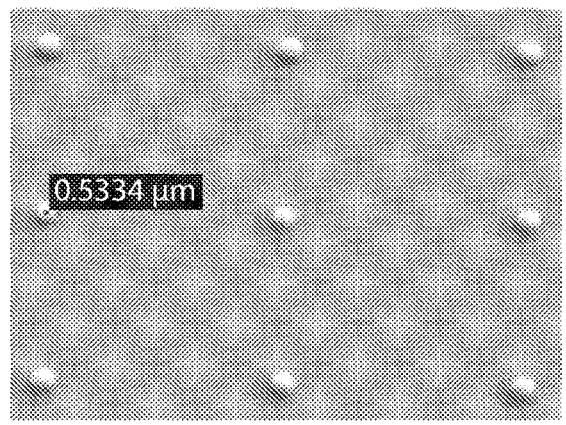
Figures 9A, 9B, 9C, 9D:
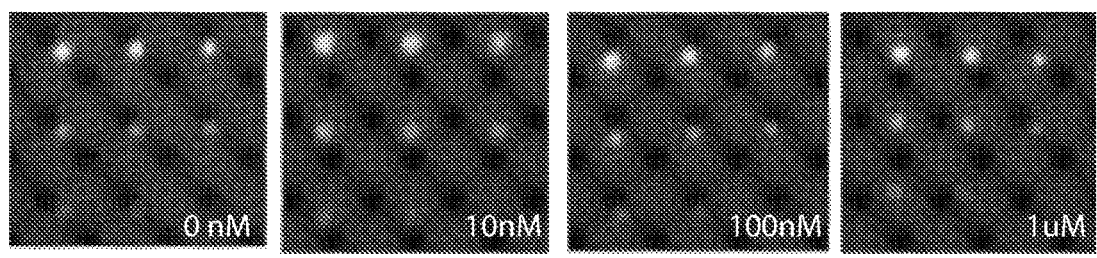
FIGS. 9A-9D show exemplary representations of the shift of color tone of nanosensors as the concentration of BSA proteins increases.

Silicon nanostructures were produced and used as label-free nanosensors. The advantage of using silicon nanostructures is that the fabrication process is complementary metal-oxide-semiconductor compatible and mass producible. The produced silicon nanostructures can be, for example, in the form of a nanorod, in which the diameter is between 50 to 300 nm and height is between 0.2 to 2 microns, as shown in FIG. 6 in this example. The color of nanorods with different diameters under a dark field image displays various colors of the spectrum (see FIGS. 7A-7B). For diameters below 250 nm, each nanorod has a distinctive color. When the diameters are larger than about 300 nm, the color spectrum becomes similar. The silicon nanostructures can also take other forms, such as cones, needles, wires, and particles, as shown in FIGS. 8A-8D. The dimensions used range from 50 nm to 1 micrometers.

To test the sensitivity of the silicon nanorod, the chip or microwell array was functionalized with 2% APTM solution in ethanol (v/v) for 20 minutes. Next, 10 mM glutaraldehyde, 10 mM sodium cyanoborohydride, and 1/1000 diluted anti-BSA was dropped onto the microwell array, which was then incubated for 2 hours. The microwell array was then rinsed. Different concentrations of BSA solutions were dropped onto the nanosensor. The microwell array was washed in deionized waster and imaged under a dark field microscope with 20× objective. As shown in FIGS. 9A-9D, the color tone of each nanosensor shifts to red (i.e., an increase in wavelength) as the concentration of BSA proteins was increased.

EXAMPLE 2

Figure 10A:
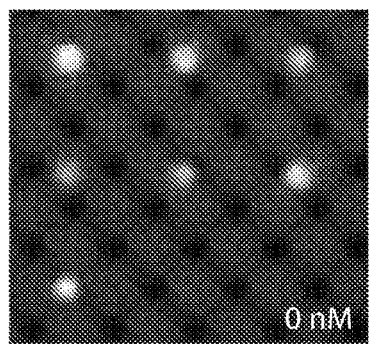
FIGS. 10A-10C show exemplary representations of the shift of color tone of nanosensors as the concentration of streptavidin increases.
Figure 10B:
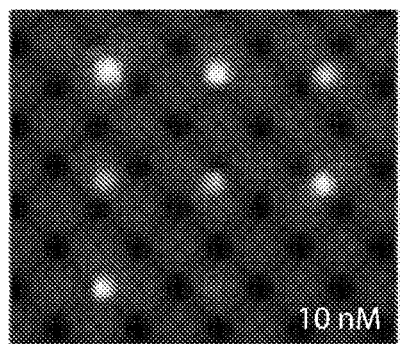
Figure 10C:
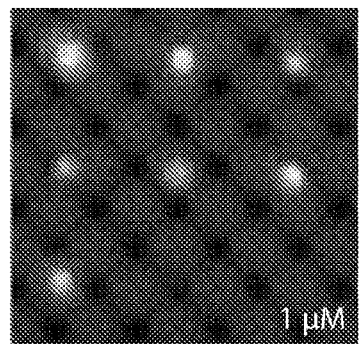
Figure 11A:
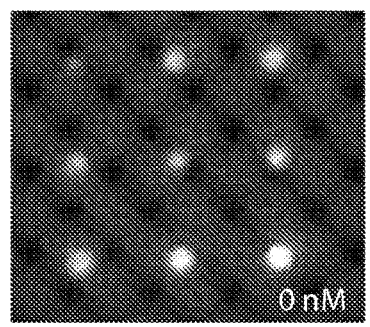
FIGS. 11A-11C show exemplary representations of the shift of color tone of nanosensors with various diameters as the concentration of streptavidin increases.
Figure 11B:
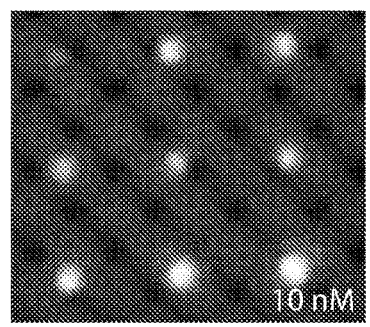
Figure 11C:
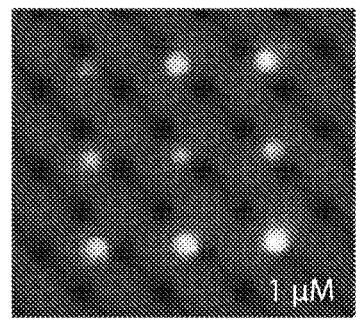

Different concentrations of streptavidin were tested in this example (see FIGS. 10A-10C). The color spectrum has a red-shift as streptavidin concentration is increased. In the case of streptavidin, each of the silicon nanosensors works separately. Therefore, nine different silicon nanorods of diameters of 80, 100, 120, 140, 160, 180, 200, 220, and 240 nm were made and their color response to different concentrations of streptavidin solutions was tested in this example, as shown in FIGS. 11A-11C. The spacing between each silicon nanosensor was 5 micrometers.

Figure 12:
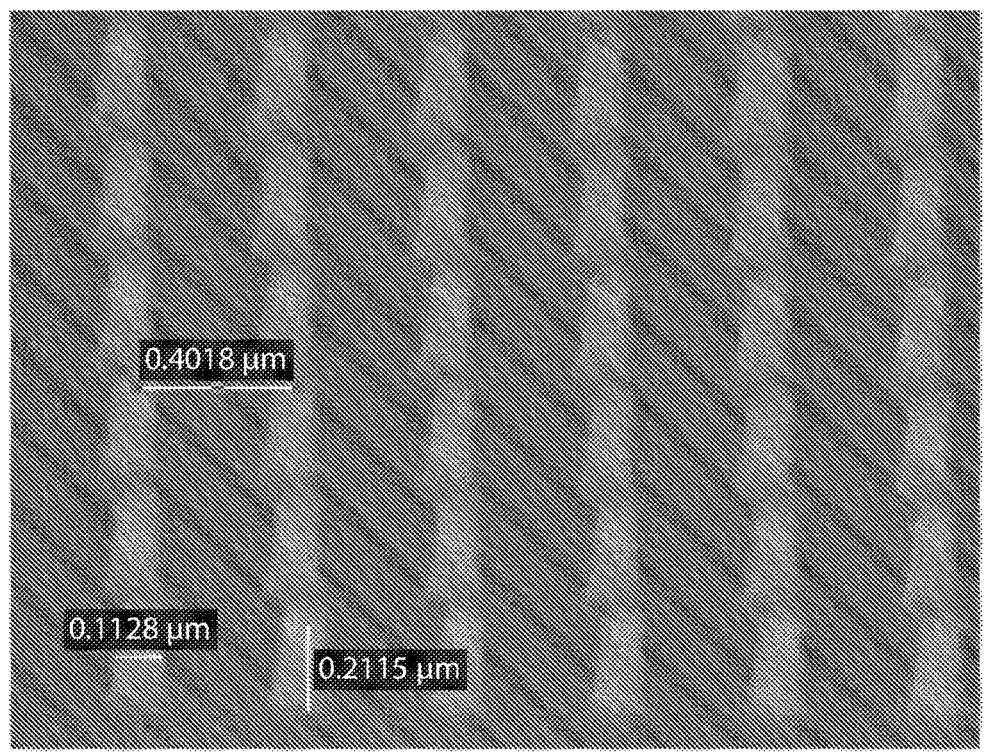
FIG. 12 shows, according to some embodiments, nanorods with ~100 nm diameter and ~400 nm spacing.
Figure 13A:
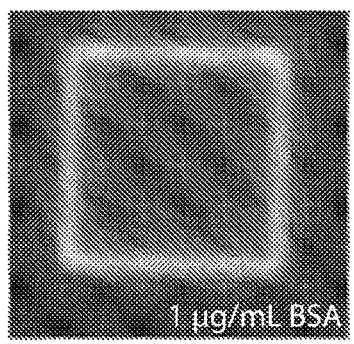
FIGS. 13A-13C show exemplary representations of the shift of color tone of ~100 nm diameters nanorods with various concentrations of BSA proteins as the proteins absorb onto the meta-surface.
Figure 13B:
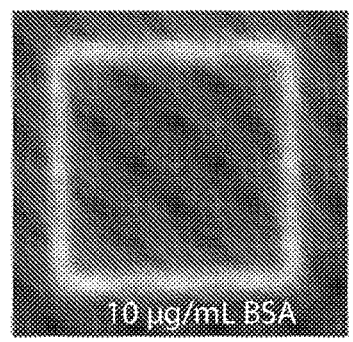
Figure 13C:
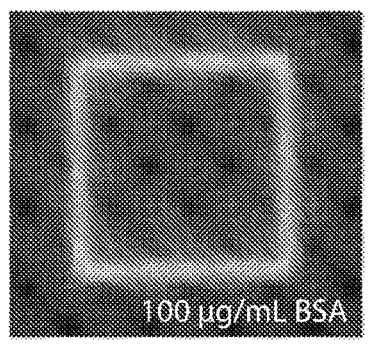

When the distance between nanosensors was decreased below the photon wavelength, the scattered light from individual nanorods interferes and collectively forms a silicon meta-surface. The meta-surface acts as sensor, which can be used to detect protein concentrations. For example, as shown in FIG. 12, when the diameter of each nanorod is ~100 nm, spacing is ~400 nm. This produces a generally green color in deionized water, and as proteins absorb into its surface, the overall color red-shifted, as shown in FIGS. 13A-13C.

Figure 14:
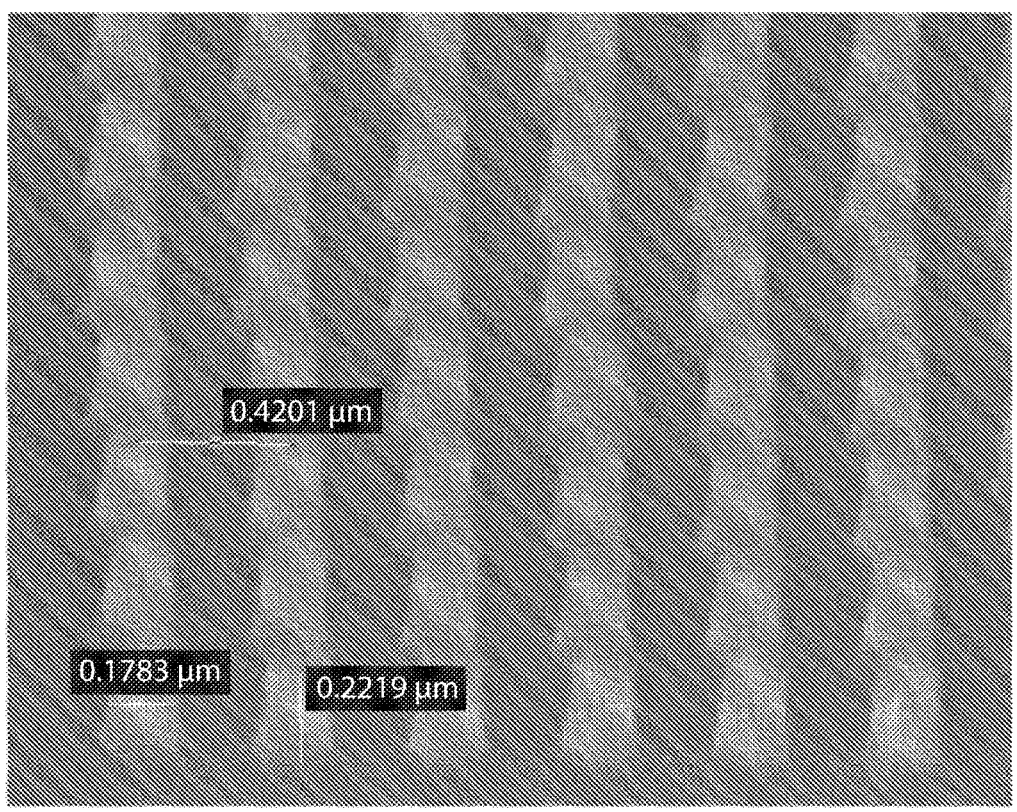
FIG. 14 shows, according to some embodiments, nanorods with ~180 nm diameter and ~420 nm spacing.
Figure 15A:
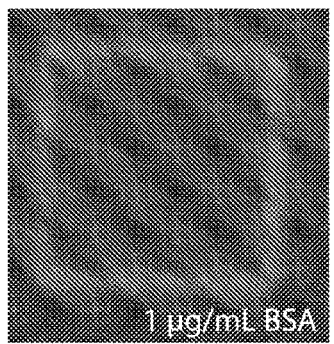
FIGS. 15A-15C show exemplary representations of the shift of color tone of ~180 nm diameter nanorods with various concentrations of BSA proteins as the proteins absorb onto the meta-surface.
Figure 15B:
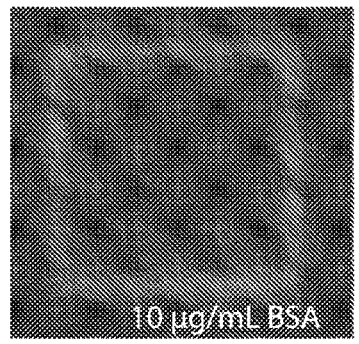
Figure 15C:
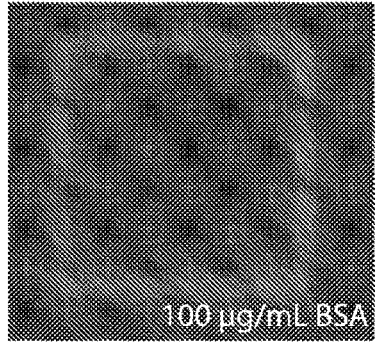
Figure 16A:
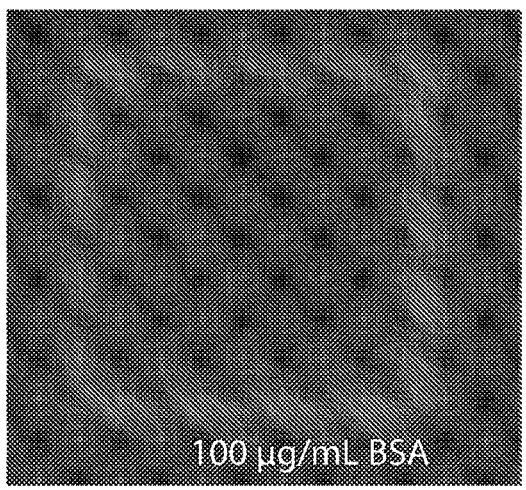
FIG. 16A-16B show exemplary representations of the shift of color tone of ~180 nm diameter nanorods with various concentrations of BSA proteins as the proteins absorb onto the meta-surface with a 1.8 nm diameter gold nanoparticle as secondary label to amplify the color shift.
Figure 16B:
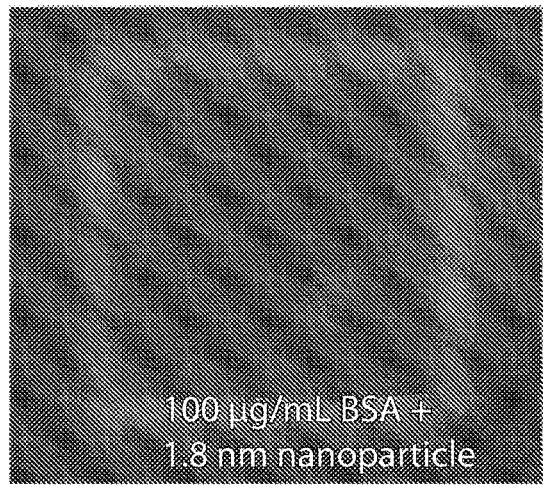

The diameter of each individual nanorod was decreased to ~180 nm (see FIG. 14), while the spacing was ~420 nm. The overall color hue was orange-green in deionized water, and red-shifted as proteins absorbed onto its surface, as shown in FIGS. 15A-15C. Furthermore, the 1.8 nm diameter gold particles functionalized with anti-BSA was used as a secondary label to amplify the color shift from the meta-surface nanosensor. The shift of the color hue due to binding of nanoparticles is an order of magnitude larger than the shift due to binding of molecular analytes (30 nm vs. 3 nm) (FIGS. 16A-16B). Color shifts such as these may be quantified, for example, using a suitable colorimetric detector.

EXAMPLE 3

Figure 17:
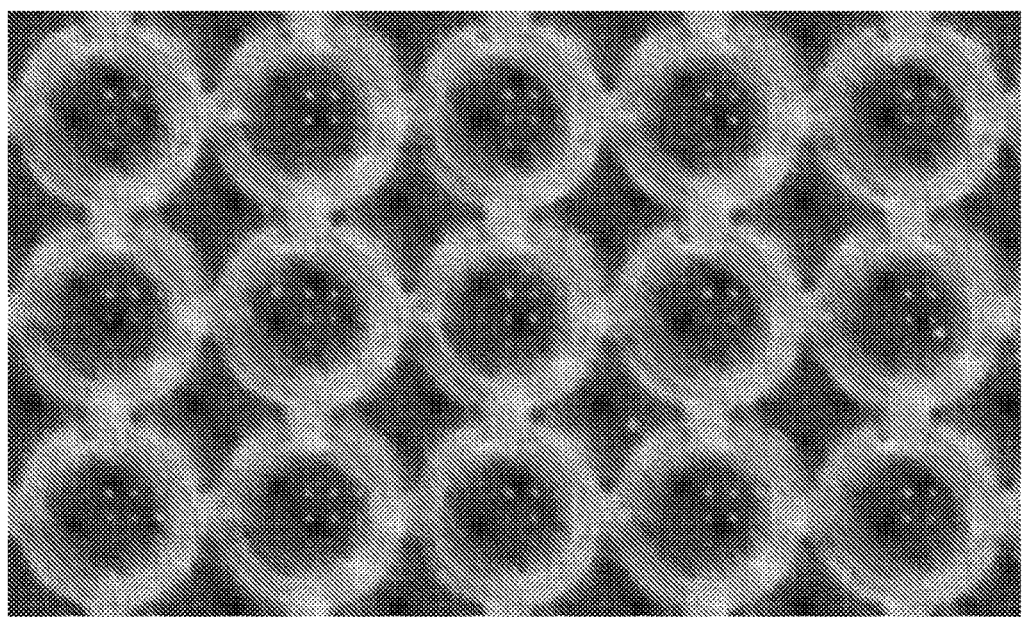
FIG. 17 shows an exemplary representation of a dark field image of the microwell array with 3×3 individual nanosensor arrays in each well.

To detect protein expressions in single cells, silicon nanosensors were fabricated on a silicon wafer using electron beam lithography and reactive ion etching in this example. A single layer of 2% 950K PMMA (A2) was used. The wafer was first dehydrated at 150° C. for 30 minutes. Next, PMMA was spun at 1600 rpm for 40 seconds, which gives a thickness of 100 nm. The wafer was pre-baked at 200° C. for 2 minutes. ELIONIX F125 was used with dosage 1800 microcoloumbs/$cm^2$ at 125 keV. The resist was developed in 1:3 methylisobutyl ketone:isopropyl alcohol (v/v) for 30 seconds and rinsed in isopropyl alcohol. The wafer was then coated with 30 nm alumina using a thermal evaporator and lifted-off in hot acetone for 3 hours. The wafer was then etched using STS-RIE for 2 minutes. The microwell array with a 3×3 individual nanosensor arrays in each well was analyzed by dark field imaging, as shown in FIG. 17. Each nanosensor in the 3×3 group had slightly different dimensions and therefore appeared to be different colors.

EXAMPLE 4

A single cell suspension (cell concentration 20,000/mL) was created and 20 microliters was dropped onto the microwell array in this example. The cells diffused into the microwells with a trapping efficiency that was sensitive to the geometry of the microwells.

Figure 18A:
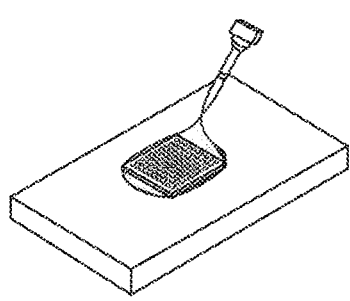
FIGS. 18A-18C show a 20 microliter droplet of a single cell suspension applied onto a sensor chip of a microwell array and a nanosensor array.
Figure 18B:
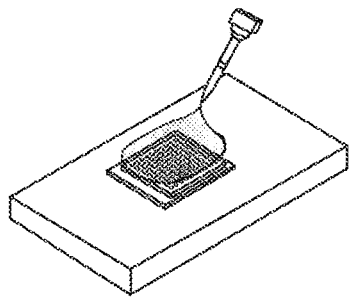
Figure 18C:
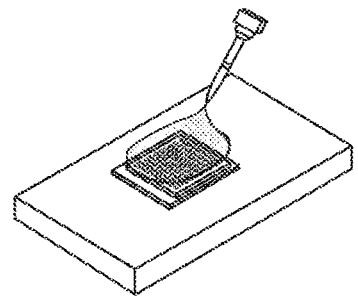
Figure 19A:
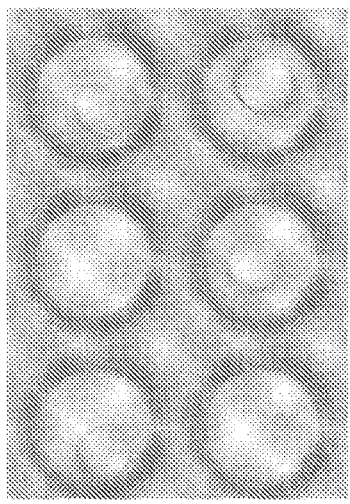
FIGS. 19A-19C shows exemplary representations of the binding of proteins on nanosensors inducing a color shift that correlates to protein concentration.
Figure 19B:
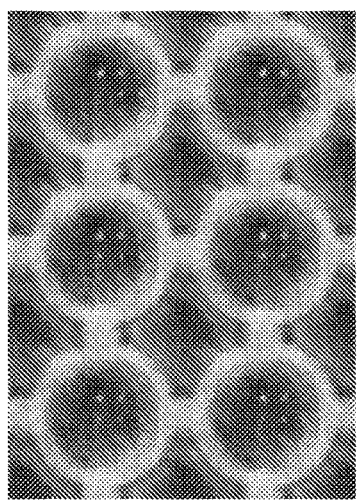
Figure 19C:
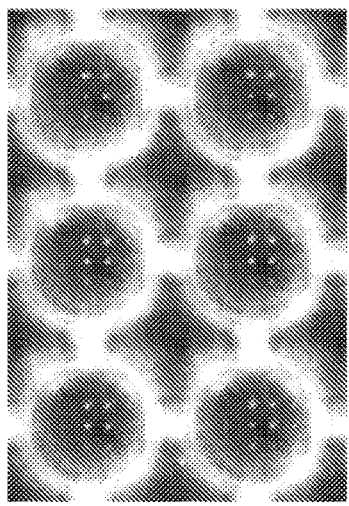

Before loading the cells onto the microwell array, the microwell array was incubated in 2% APTMS in ethanol (v/v) for 10 minutes. The microwell array was rinsed thoroughly in ethanol and blow-dried with nitrogen gas. Next, 10 mM glutaraldehyde, 10 mM sodium cyanoborohydride, and 1/1000 diluted anti-beta-actin was dropped onto the microwell array and incubated for 2 hours. The microwell array was then rinsed with deionized water. A droplet (20 microliters) of the single cell suspension was applied onto the sensor chip, which had both the microwells and nanosensors, as shown in FIGS. 18A-18C. After seeding the cells on the chip for 10 minutes, a hydrophilic semi-permeable membrane (polycarbonated membrane with 10 nm pore size, 6 micron thickness) was applied onto the microwell array. The membrane sealed the surface due to the hydrophilicity. Next, a droplet of cell lysis buffer was applied on the membrane, passing through into the individual microwells. The cells were lysed within individual microwells and target proteins were captured by the nanosensors. Binding of proteins on the nanosensors induced a color shift, which correlated with the protein concentrations, are shown in FIGS. 19A-19C.

EXAMPLE 5

Figure 20:
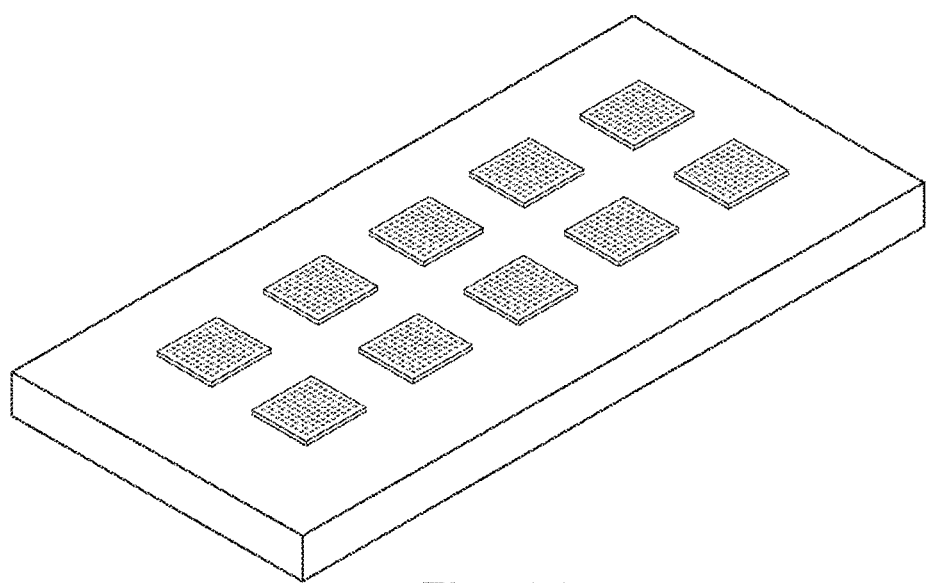
FIG. 20 shows, according to some embodiments, a 75 mm×25 mm glass slide with 10 microwell arrays.

To detect multiple proteins from single cells, multiple microwell arrays were integrated onto a glass slide in this example. A single microwell array had a size of 1 cm×1 cm, containing 1000 cell traps, with nanosensors integrated inside each microwell. A 75 mm×25 mm glass slide hosted 10 microwells, as shown in FIG. 20. Each microwell was functionalized with a different antibody. A glass slide with 10 microwells can therefore detect 10 different proteins in 10 groups of 1000 single cells.

Figure 21A:
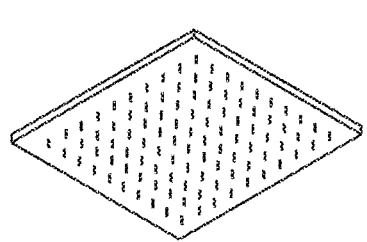
FIGS. 21A-21C show exemplary representations of nanosensors on top of silicon nano- or micro-sized needles spaced at the same periodicity as microwells.
Figure 21B:
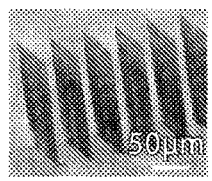
Figure 21C:
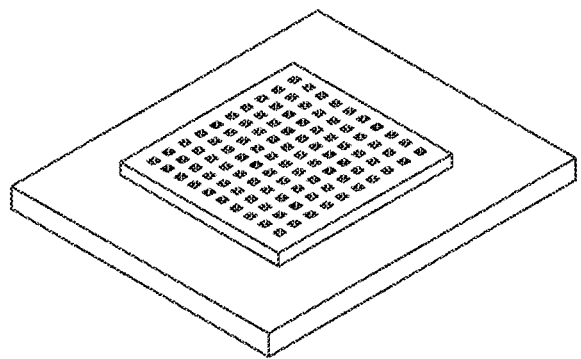

To detect multiple proteins in the same group of single cells, nanosensors were fabricated on top of silicon nano- or micro-sized needles. The nanosensors used gold, silver, or silicon. The nanoneedles were spaced at the same periodicity as the microwells (see FIGS. 21A-21C). Therefore, each nanoneedle could be aligned with each microwell. The nanosensors on top of each nanoneedle detected the protein concentration in the cell lysis from each microwell. To analyze multiple proteins from the same group of single cells, different nanoneedles functionalized with different antibodies were sequentially brought in contact with the same microwell array.

EXAMPLE 6

When the analyte in solution reaches the sub-pM concentration level, only a maximum number of one analyte molecule will be available to bind each individual nanosensor, while most nanosensors in the array do not have any molecules bound. In this detection regime, a threshold level of the signal (e.g., color change, fluorescence) from the nanosensor can be assigned as either 1 or 0. The concentration of the analyte in the solution can be derived from directly counting the number of nanosensors that has a signal assignment of 1, therefore suppressing the noise signal inherent to traditional bulk colorimetry or fluorescence measurements at the ultra-low concentrations.

Figures 22A, 22B, 22C:
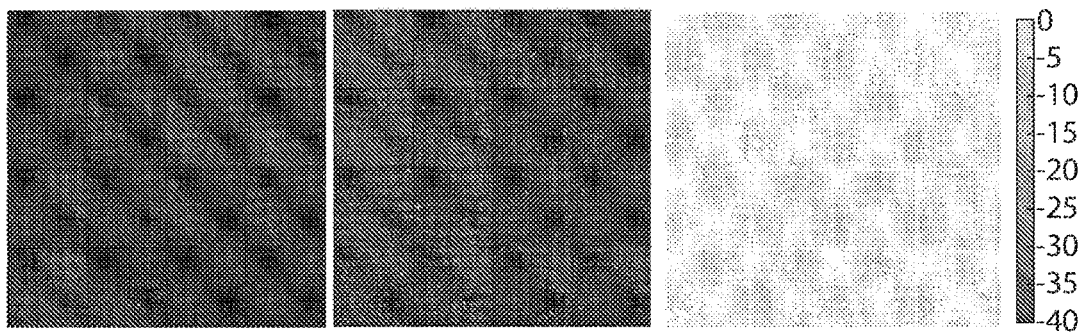
FIGS. 22A-22I show exemplary representations of nanosensor arrays for detecting protein concentrations of 0.1 to 10 pM.

Since nanosensor arrays have a typical pitch in the range of 1-10 micrometers, it is possible to densely pack 10,000 to 1,000,000 nanosensors in a small area (e.g., 1 mm by 1 mm). FIGS. 22A-22I illustrate the optical signal of nanosensor arrays under this regime. In FIG. 22A-22I, 16 blocks of nanosensor arrays were fabricated on a silicon chip. Each block has a matrix of 32 by 32 nanosensors, spacing at 2 micrometers. Each nanosensor has a nanorod shape, with a diameter of 95 nm and a length of 200 nm. FIG. 22A shows the chip under dark field imaging, where each nanosensor shows a green scattering spot, collected by a color camera. The nanochip was functionalized with 2% (3-aminopropyl) trimethoxysilane (APTMS) in 95% ethanol for 10 minutes, and washed with ethanol, heated at 80° C. for 2 hours.

The chip was then functionalized with 10 mM of glutaraldehyde and 10 mM of sodium cyanoborohydride for 1 hour. The sensor surface was coated with 1 microgram/ml tau proteins. Different concentrations of anti-tau proteins were then flowed on to the chip as the detection targets. The anti-tau protein was prepared in a PBS buffer solution containing 0.1% gelatin and 150 mM NaCl. The anti-tau protein was horseradish peroxidase labeled. After reacting with chromogenic substrate, a layer of non-soluble deposit was formed on the nanosensor surface, creating an optical resonance change of the nanosensor.

Figures 22D, 22E, 22F:
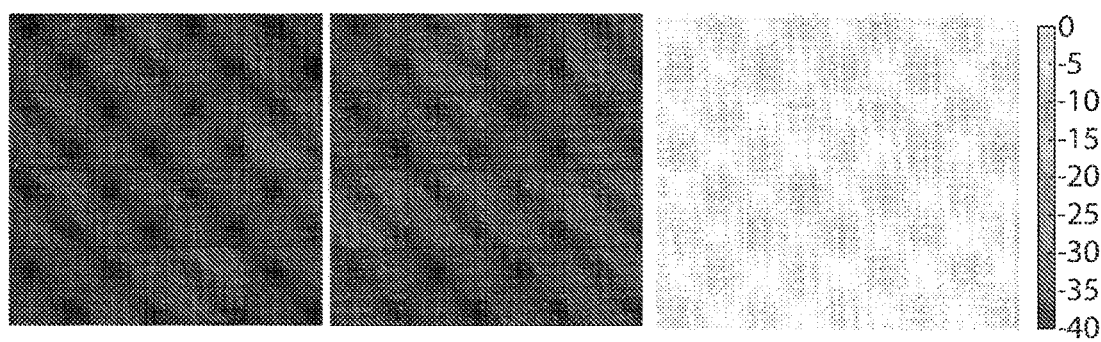
Figures 22G, 22H, 22I:
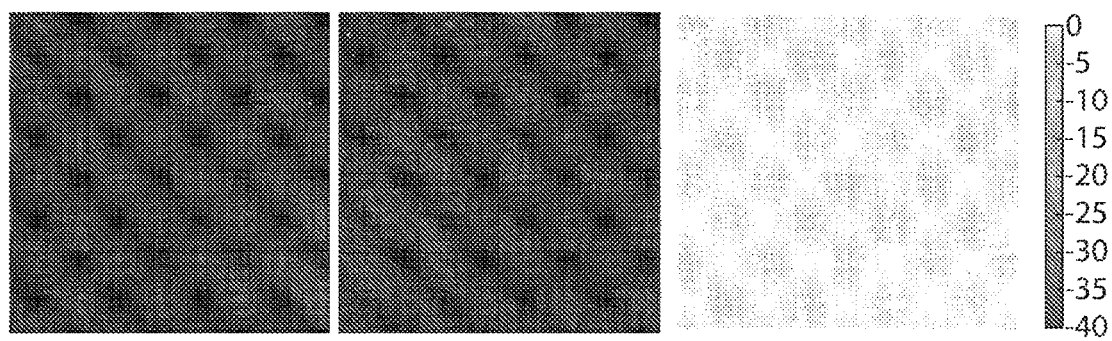

FIG. 22B shows the dark field image after the assay, where each nanosensor has changed color from green to yellow when detecting proteins capture by antibodies functionalized on the nanosensor. FIG. 22C shows the extracted hue change from aligning FIG. 22A and FIG. 22B and subtracting the corresponding spots. At 10 pM anti-tau protein concentration, every nanosensor in FIG. 22C displayed a delta-hue at about −40. FIGS. 22D-22F show embodiments where the anti-tau protein concentration was decreased to 1 pM, and FIGS. 22G-22I show embodiments where the anti-tau protein concentrations were decreased to 0.1 pM. A subset of the nanosensors had observable delta-hue in FIGS. 22D-22F. As shown in FIGS. 22G-22I, most nanosensors do not have observable delta-hue, indicating that most nanosensors do not have proteins bound on their surface.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    allowing a lysing reagent to enter a well of a microwell array through a semipermeable membrane sealing the well, wherein the semipermeable membrane is configured to prevent a lysate from leaving the well;
    lysing a cell within the well to release an analyte suspected of being able to bind a reaction entity;
    applying electromagnetic radiation to a nanoparticle at least partially coated with the reaction entity, wherein: (i) the nanoparticle is configured to interact with the electromagnetic radiation via electric resonance and/or magnetic resonance to alter the electromagnetic radiation; and (ii) the well comprises a nanostructure and the nanoparticle is positioned distally on an end of the nanostructure; and
    determining the altered electromagnetic radiation.

2. A method, comprising:
    acquiring a first optical color image of an array of nanostructures on a substrate, wherein the nanostructures have a cross-sectional dimension, orthogonal to the direction that the first optical image is acquired, of less than 700 nm, wherein: (i) the nanostructures are at least partially coated with a reaction entity; (ii) the substrate comprises a microwell array comprising a plurality of wells, each well comprising a nanostructure of the array of nanostructures; and (iii) the nanostructures are attached to the substrate;
    allowing a lysing reagent to enter a well of the plurality of wells through a semipermeable membrane sealing the well, wherein the semipermeable membrane is configured to prevent a lysate from leaving the well;
    lysing a cell within the well to release an analyte suspected of being able to bind the reaction entity;
    causing an interaction between the reaction entity and the analyte;
    acquiring a second optical color image of the array of nanostructures; and
    determining a change in color between the first optical image and the second optical image, wherein the change in color is caused by the interaction between the reaction entity and the analyte.

3. The method of claim 1, wherein the semipermeable membrane comprises polycarbonate.

4. The method of claim 1, wherein the semipermeable membrane has a pore size of 10 nm.

5. The method of claim 1, wherein the electromagnetic radiation comprises visible light.

6. The method of claim 1, further comprising determining the reaction entity by the determined altered electromagnetic radiation.

7. The method of claim 2, wherein the array of nanostructures has an average spacing between nanostructures of less than about 3 micrometers.

8. The method of claim 2, wherein the array of nanostructures has an average spacing between nanostructures of less than about 500 nm.

9. The method of claim 2, wherein the reaction entity comprises an antibody.

10. The method of claim 2, wherein the reaction entity comprises an aptamer.

11. The method of claim 2, wherein the reaction entity comprises a protein.

12. The method of claim 2, wherein the reaction entity comprises an oligonucleotide.

13. The method of claim 2, wherein the reaction entity comprises an enzymatic reaction product induced by a chromogenic substrate labeled on the analyte.

14. The method of claim 13, wherein the chromogenic substrate is 3,3',5,5'-tetramethylbenzidine.

15. The method of claim 13, wherein the chromogenic substrate is 3,3'-diaminobenzidine.

16. The method of claim 13, wherein the chromogenic substrate is 2,2'-azino-di-(3-ethylbenzothiazoline-6-sulfonic acid).

17. The method of claim 2, wherein the nanostructure has a length of less than about 5 micrometers.

18. The method of any one of claims 2, wherein the nanostructure has a length of at least about 0.01 micrometers.

19. The method of claim 2, wherein the nanostructure comprises a semiconductor.

20. The method of claim 2, wherein the nanostructure comprises silicon.

21. The method of claim 2, wherein the nanostructure consists essentially of silicon.

\* \* \* \* \*